US010417926B2

(12) United States Patent
Bachani

(10) Patent No.: US 10,417,926 B2
(45) Date of Patent: Sep. 17, 2019

(54) BIOFEEDBACK VIRTUAL REALITY SYSTEM AND METHOD

(71) Applicant: Merlin Digital General Trading LLC, Dubai (AE)

(72) Inventor: Suhail Hiro Bachani, Dubai (AE)

( * ) Notice: Subject to any disclaimer, the term of this patent is extended or adjusted under 35 U.S.C. 154(b) by 0 days.

(21) Appl. No.: 15/523,495

(22) PCT Filed: Feb. 16, 2016

(86) PCT No.: PCT/IB2016/000143
§ 371 (c)(1),
(2) Date: May 1, 2017

(87) PCT Pub. No.: WO2016/189370
PCT Pub. Date: Dec. 1, 2016

(65) Prior Publication Data

US 2018/0075764 A1 Mar. 15, 2018

Related U.S. Application Data

(60) Provisional application No. 62/240,004, filed on Oct. 12, 2015, provisional application No. 62/166,720, filed on May 27, 2015.

(51) Int. Cl.
*G09B 19/00* (2006.01)
*G09B 5/06* (2006.01)
(Continued)

(52) U.S. Cl.
CPC ............ *G09B 5/065* (2013.01); *A61B 5/0024* (2013.01); *A61B 5/02438* (2013.01);
(Continued)

(58) Field of Classification Search
CPC ..................................................... G09B 5/065
(Continued)

(56) References Cited

U.S. PATENT DOCUMENTS

2002/0128541 A1 9/2002 Kim et al.
2014/0288614 A1 9/2014 Hagedorn et al.
(Continued)

OTHER PUBLICATIONS

Ng, "International Search Report and Written Opinion of the International Searching Authority", regarding International Application No. PCT/IB2016/000143.

*Primary Examiner* — Kesha Frisby
(74) *Attorney, Agent, or Firm* — Justin W. McCabe, Esq.; Shawn Gordon, Esq.; Dunkiel Saunders Elliott Raubvogel & Hand, PLLC

(57) ABSTRACT

The present disclosure relates to optimizing an individual's heart-rate cycle using a biofeedback virtual reality system so as to facilitate coherence and resonance, by which a subject's emotional state, stress levels and performance may be concurrently improved. In an embodiment, a biofeedback virtual reality system and method as disclosed herein accesses an individual's current coherence state and based upon that analysis, provides a virtual environment related to the individual's current coherence state and allows the individual to progress to alternative virtual environments that represent "better" or more coherent states. A biofeedback virtual reality system can include a heart monitor and an RR interval monitor that provide information related to the individual's HRV. A biofeedback virtual reality system can be conveniently portable and therefore used at most any location so as to afford the individual the ability to decrease their stress level and/or improve their state of mind as desired.

20 Claims, 8 Drawing Sheets

(51) Int. Cl.

| | |
|---|---|
| ***G16H 40/63*** | (2018.01) |
| ***G16H 50/30*** | (2018.01) |
| ***A61B 5/16*** | (2006.01) |
| ***A61B 5/00*** | (2006.01) |
| ***G06F 3/01*** | (2006.01) |
| ***G09B 5/12*** | (2006.01) |
| ***A61B 5/024*** | (2006.01) |
| ***G06F 19/00*** | (2018.01) |
| ***G16H 50/20*** | (2018.01) |
| *A61B 5/0408* | (2006.01) |
| *A61B 5/0456* | (2006.01) |
| *A61B 5/08* | (2006.01) |

(52) U.S. Cl.

CPC .............. *A61B 5/165* (2013.01); *A61B 5/486* (2013.01); *A61B 5/742* (2013.01); *A61B 5/7445* (2013.01); *G06F 3/015* (2013.01); *G06F 19/3481* (2013.01); *G09B 5/125* (2013.01); *G09B 19/00* (2013.01); *G16H 40/63* (2018.01); *G16H 50/20* (2018.01); *G16H 50/30* (2018.01); *A61B 5/0006* (2013.01); *A61B 5/02405* (2013.01); *A61B 5/0456* (2013.01); *A61B 5/04085* (2013.01); *A61B 5/0816* (2013.01); *A61B 5/6803* (2013.01); *A61B 5/6831* (2013.01); *A61B 5/6898* (2013.01); *G06F 19/3418* (2013.01)

(58) Field of Classification Search

USPC .......................................................... 434/236

See application file for complete search history.

(56) References Cited

U.S. PATENT DOCUMENTS

2014/0316192 A1 10/2014 De Zambotti et al.
2014/0350431 A1 11/2014 Hagedorn

BIOFEEDBACK VIRTUAL REALITY SYSTEM AND METHOD

RELATED APPLICATIONS

This application is a national stage application of PCT Application No. PCT/IB2016/000143, filed Feb. 16, 2016 and titled "BIOFEEDBACK VIRTUAL REALITY SYSTEM AND METHOD," which claims priority to U.S. Provisional Application No. 62/240,004, filed Oct. 12, 2015, and entitled "BIOFEEDBACK VIRTUAL REALITY SYSTEM AND METHOD" and to U.S. Provisional Application No. 62/166,720, filed May 27, 2015, and entitled "Virtual reality based heart rate variability coach and tracker", each of which is incorporated by reference in their entirety.

FIELD OF THE INVENTION

The present disclosure generally relates to the field of physiological biofeedback systems. In particular, the present disclosure is directed to an improved heartrate biofeedback virtual reality system and method.

BACKGROUND

An individual's heart rate can have large impacts on the individual's health. It is well known that an individual's heart rate adapts to changes in the body's need for oxygen, which can be precipitated by exercise, rest, or other levels of activity. A change in heart rate also occurs in response to stressful stimuli, resulting from a release of adrenaline and cortisol, and concomitant with the heart rate increase is a redirection in blood flow to the muscular system, fat releases into the bloodstream for use as energy, increases in breathing rate, muscle tension, and increases in blood clotting ability. While these reactions may be beneficial in a fight-or-flight situation, these situations are uncommon; instead individuals are engaged in prolonged periods of stress caused by work, family, children, etc., that negatively affect their health.

Biofeedback techniques have been used to self-regulate heart rate. In general, biofeedback is a process that trains an individual to influence involuntary physiological functions for the purposes of improving health and performance. As some examples, biofeedback techniques have purportedly been used to treat migraine and tension headaches, digestive disorders, hypertension, hypotension, cardiac arrhythmia, Raynaud's, epilepsy, paralysis, movement disorders and chronic pain.

Evaluation of an individual's heart rate is typically done via a few different methodologies. A standard heart rate measurement is simply an assessment of the number of heart beats per unit of time, typically beats per minute (BPM). A more accurate, yet more difficult to measure, metric, is heart rate variability (HRV). HRV monitoring involves monitoring the heart beat rate and discerning the rate at which the heart beat rate changes. HRV may be monitored by detecting the individual's pulse and measuring the inter-beat interval (the "rise-rise interval" or RR interval).

SUMMARY OF THE DISCLOSURE

In a first exemplary aspect a biofeedback virtual reality system is disclosed, the biofeedback virtual reality system comprising a virtual reality headset having a viewing area for a user; a sensor capable of producing a signal indicative of a physiological parameter of the user; a portable computing device coupled to the virtual reality headset and electronically coupled to the sensor, the portable computing device capable of receiving the signal and including a processor and a memory, the memory including a plurality of virtual reality environments and a set of instructions executable by the processor, the instructions including; determining the mental state of the user based upon the signal; delivering a selected one of the plurality of environments to a user; adjusting the selected one based upon the determining, wherein the adjusting is in the form of setting a plurality of initial conditions associated with the selected one of the virtual reality environments; monitoring the signal; and altering the selected one of the plurality of environments based upon the monitoring.

In another exemplary aspect a biofeedback virtual reality system is disclosed, the biofeedback virtual reality system comprising a sensor capable of producing a first signal representative of a user's heart rate and of producing a second signal representative of the time between heart beat peaks of the user; and a virtual reality device including a headset and a portable computing device coupled to the virtual reality headset and electronically coupled to the sensor, the portable computing device capable of receiving the signal and including a processor and a memory, the memory including a plurality of virtual reality environments and a set of instructions executable by the processor, the instructions including; determining the mental state of the user based upon the first signal and the second signal; delivering a selected one of the plurality of environments to a user; adjusting the selected one based upon the determining, wherein the adjusting is in the form of setting a plurality of initial conditions associated with the selected one of the virtual reality environments; monitoring the first signal and the second signal; and altering the selected one of the plurality of environments based upon the monitoring.

In yet another exemplary aspect a method of improving a mental state of a user in need thereof is disclosed, the method comprising providing a virtual reality device and a sensor capable of transmitting a signal representative of physiological information of the user, the virtual reality device including a plurality of virtual reality environments; determining a current mental state of the user based upon the signal; setting an initial state of a selected one of the plurality of virtual reality environments based upon the determining; providing a breath indicator, the breath indicator indicating when the user should attempt to take a breath; monitoring the mental state of the user via the plurality of sensors; adjusting the state of the selected one of the plurality of virtual reality environments, from the initial state, based upon the monitoring.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DESCRIPTION OF THE DISCLOSURE

Figure 1:
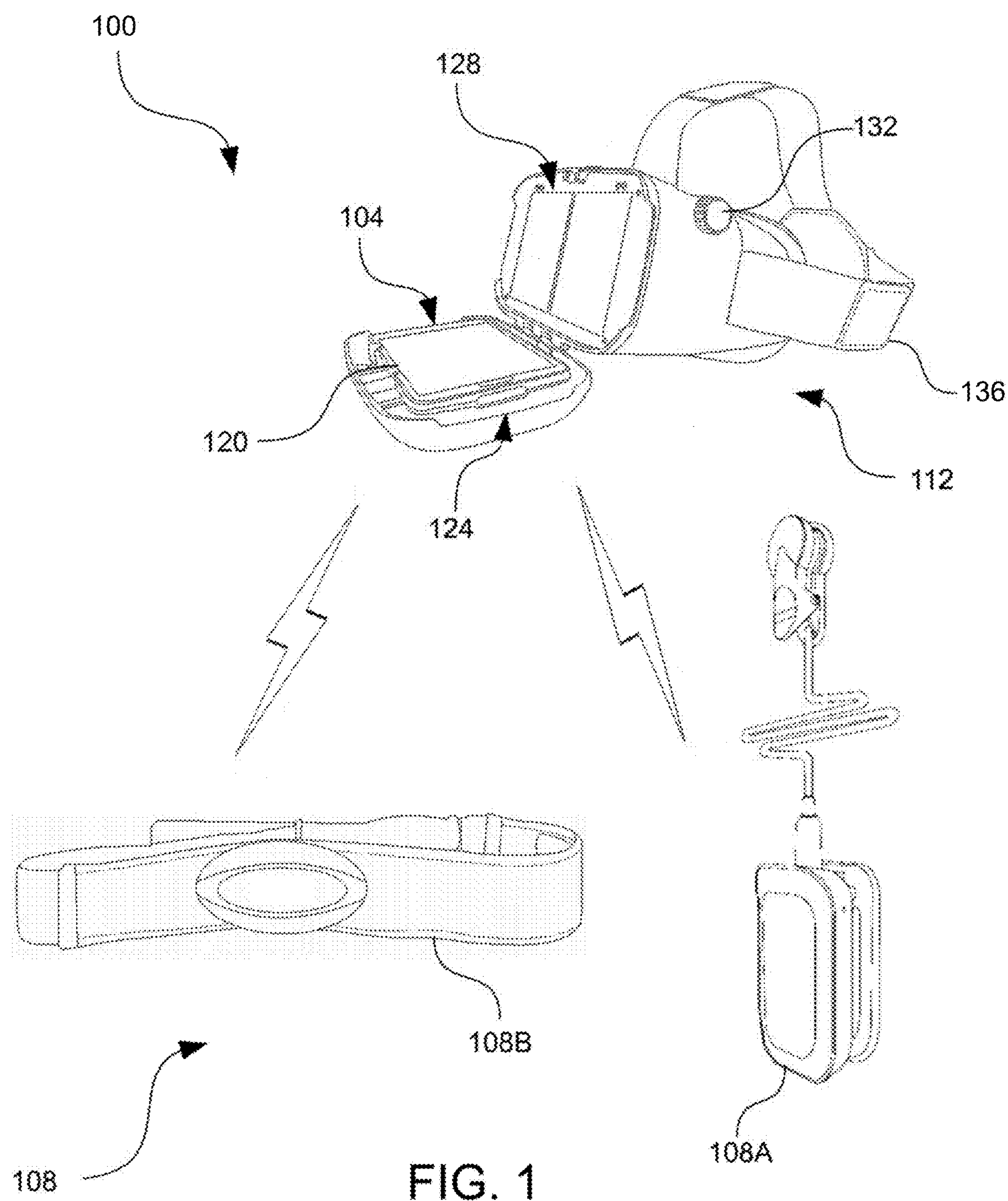
FIG. 1 is a perspective view of a biofeedback virtual reality system according to an embodiment of the present invention.

A biofeedback virtual reality system and method of the present disclosure relates to optimizing an individual's heart-rate cycle using a biofeedback virtual reality system so as to facilitate coherence and resonance, by which a subject's emotional state, stress levels, and performance may be concurrently improved. In an embodiment, a biofeedback virtual reality system and method as disclosed herein assesses an individual's current coherence state and based upon that analysis, provides a virtual environment directly related to the individual's current coherence state and allows the individual to progress to alternative virtual environments that represent "better" or more coherent states (or if regression is shown, the virtual environment can move to a representation of "worse" coherent states). A biofeedback virtual reality system can include a heart rate monitor that provides information related to, among other things, the individual's heart rate variability (HRV). A biofeedback virtual reality system can be conveniently portable and therefore used at most any location so as to afford the individual the ability to decrease their stress level and/or improve their state of mind as desired. A biofeedback virtual reality system can also include a competition component that challenges the user to obtain a higher score or where the user can compete with other individuals using the biofeedback virtual reality system disclosed herein.

According to certain embodiments of the present disclosure, a biofeedback virtual reality system is disclosed that includes a virtual reality (VR) head-mounted display, a control system, and a sensor, such as a heart rate monitor (HRM) (such as a Bluetooth-based chest strap or ear-clip sensor) for monitoring an individual's physiological parameter (heart rate) while presenting the individual with an immersive VR environment that changes over time following changes in the values of the physiological parameter. The changes in the immersive VR environment are configured using biofeedback technology and are designed to train the individual to achieve a more relaxed state of being or coherence. By placing an individual in a virtual reality environment and using biofeedback technology to provide simple breathing instructions, the biofeedback virtual reality system can provide audio and visual changes to the virtual reality environment in order to improve the individual's emotional state and heart rate variability, thereby helping the individual enter a state of relaxation.

The term "coherence," as used herein, broadly describes more ordered mental and emotional processes as well as more ordered and harmonious interactions among various physiological systems. As such, coherence can embrace many other terms, such as synchronization, entrainment, and resonance, that are used to describe the ordering of one or more of the aforementioned processes. Physiological coherence is associated with increased coherence in breathing rhythms and the heart's rhythmic activity, which manifests as a sine wave-like heart rhythm pattern (referred to as autocoherence), and an increase in entrainment among different physiological oscillatory systems, including, but not limited to, the heart rhythms, respiratory rhythms, and blood pressure waves.

Resonance also occurs during physiological coherence. For example, when an individual has increased coherence, synchronization can occur between the sympathetic and parasympathetic branches of the autonomic nervous system, and entrainment can occur among various body rhythms, such as, but not limited to, heart rhythms, respiratory rhythms, blood pressure oscillations, low-frequency brain rhythms, and craniosacral rhythms. As the aforementioned systems all vibrate at the resonant frequency of the system, e.g., about 0.1 Hertz, when the individual is physiologically coherent, the power spectrum of the heart rhythm displays an unusually large peak around 0.1.

In terms of physiological functioning, physiological coherence can confer a number of benefits. For example, studies have shown that there is increased cardiac output in conjunction with an increased efficiency in fluid exchange, filtration, and absorption between the capillaries and tissues; an increased ability of the cardiovascular system to adapt to circulatory requirements; and an increased temporal synchronization of cells throughout the body. Moreover, there is a link between positive emotions and increased physiological efficiency, which may partly explain the growing number of correlations documented between positive emotions, improved health, and increased longevity.

Turning now to the figures, and particularly, FIG. 1, there is shown a biofeedback virtual reality system (BVRS) 100 according to an embodiment of the present disclosure. At a high level, BVRS 100 includes a portable computing device 104, a sensor 108, and a virtual reality headset 112.

Generally, portable computing device 104 is capable of assessing an individual's state of mind and/or stress level and producing a training platform to enable the user to improve their state of mind and/or lower their stress level. More specifically, portable computing device 104 is configured to receive a signal representative of information related to the heart rate and RR interval of the individual using BVRS 100. Portable computing device 104 can assess the heart rate and RR interval information of the individual by, for example, comparing the individual's information to the individual's historic heart rate and/or RR interval data, to other similar individual's information, to scientific studies of similar persons' data, or other available comparative information. In an exemplary embodiment, one or more modules or sets of instructions are installed in portable computing device 104 so as to facilitate the activities discussed above and/or to carry out one or more of the processes described herein.

Portable computing device 104 develops a training platform, discussed in more detail below, for the individual based upon HRV information, which is derived from information received from sensor 108, and runs the training platform for the individual. In an exemplary embodiment, portable computing device 104 can be, but is not limited to, a smartphone, smartwatch, tablet, portable computer, virtual reality player, or other mobile device that can be easily transported by an ordinary person. As shown in FIG. 1, portable computing device 104 is a mobile device 120 that can be mounted within virtual reality headset 112.

Figure 2:
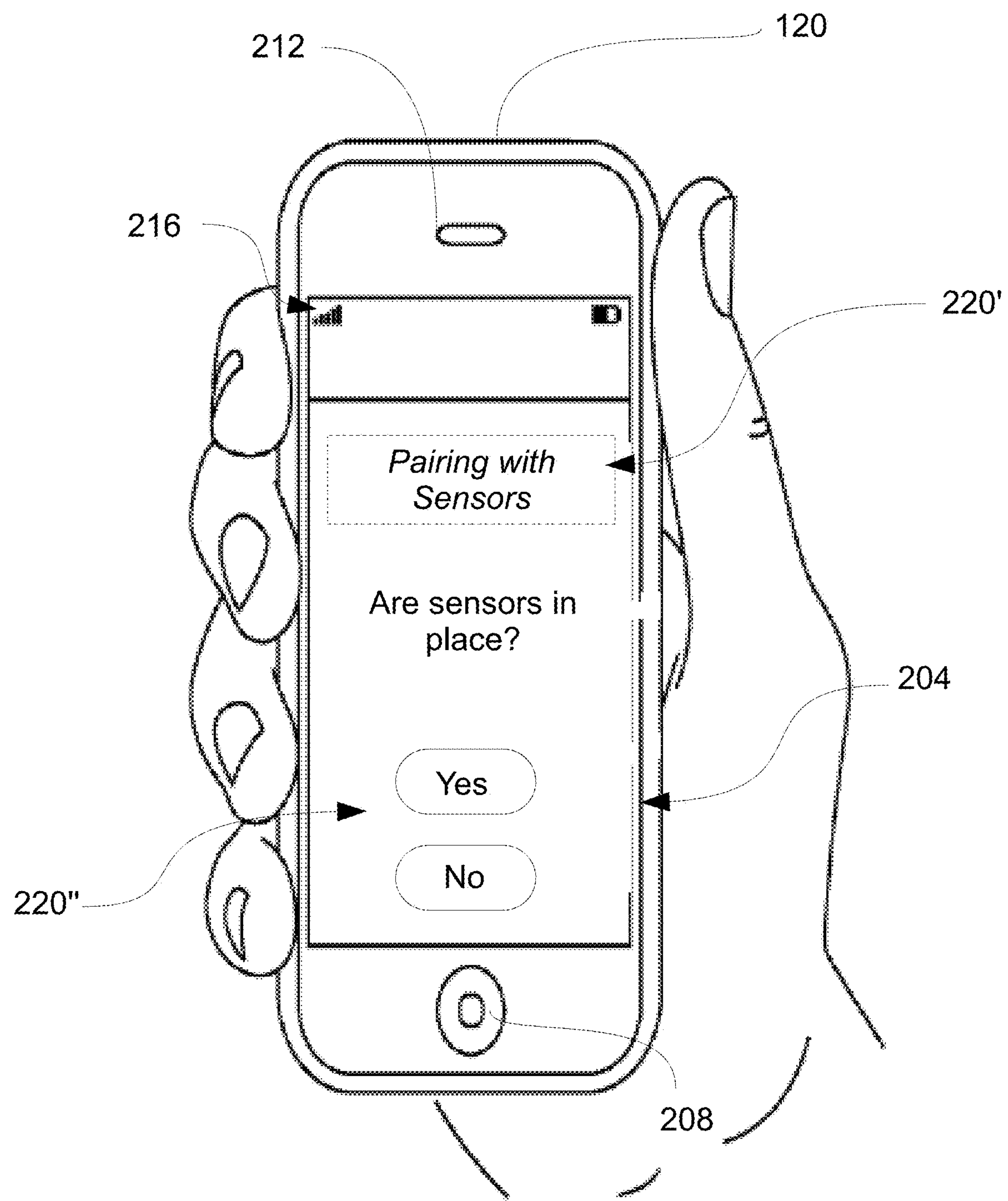
FIG. 2 is a perspective view of a portable computing device according to an embodiment of the present invention.

Turning now to FIG. 2, there is shown an implementation of a mobile device 120 suitable for use with BVRS 100. Mobile device 120 can include a touch-sensitive display 204, an input device 208, a speaker 212, and a transceiver 216. Touch-sensitive display 204 is sometimes called a "touch screen" for convenience, and may also be known as or called a touch-sensitive display system. Touch screen 204 can be used to display information or to provide individual-interface objects 220 (e.g., virtual (also called "soft") control keys, such as buttons or keyboards), thereby providing an input interface and an output interface between mobile device 120 and an individual. Information displayed by touch screen 204 can include graphics, maps, text, icons, video, and any combination thereof (collectively termed "graphics"). In an embodiment, and in use with BVRS 100, an individual can select one or more individual-interface objects 220 using touch screen 204 to select a desired virtual reality scene (discussed in more detail below).

Touch screen 204 has a touch-sensitive surface, which uses a sensor or set of sensors to accept input from the individual based on haptic and/or tactile contact. Touch screen 204 may use LCD (liquid crystal display) technology, or LPD (light emitting polymer display) technology, although other display technologies suitable for displaying virtual reality or immersive environments may be used in other embodiments. Touch screen 204 can detect contact (and any movement or breaking of the contact) on the touch screen and converts the detected contact into interaction with individual-interface objects (e.g., one or more soft keys, icons, web pages or images) that are displayed on the touch screen. Touch screen 204 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 204. In an exemplary embodiment of the use of mobile device 120, an individual presses a finger to touch screen 204 so as to initiate contact. In alternative embodiments, an individual may make contact with touch screen 204 using any suitable object, such as, but not limited to, a stylus.

Input device 208 facilitates navigation among and interacts with one or more individual-interface objects 220 displayed in the touch screen 204. In an embodiment, input device 208 is a click wheel that can be rotated or moved such that it can be used to select one or more user-interface objects 220 displayed on touch screen 204. In an alternative embodiment, input device 208 can be a virtual click wheel, which may be either an opaque or semitransparent object that appears and disappears on the touch screen display in response to individual interaction with mobile device 120. In yet other embodiments, input device 208 may be one or more sensors that are configured to respond to movement of the user's eyes, and, in that vein, certain eye movements by the user may prompt certain responses that result in changes on touch screen 204 or to the operation of mobile device 120.

Transceiver 216 receives and sends signals from mobile device 120. In an embodiment of mobile device 120, transceiver 216 sends and receives radio frequency signals through one or more communications networks, such as network 844 (FIG. 8), and/or other computing devices. Transceiver 216 may be combined with well-known circuitry for performing these functions, including, but not limited to, an antenna system, one or more amplifiers, a tuner, one or more oscillators, a digital signal processor, a CODEC chipset, a subscriber identity module (SIM) card, and a memory. As mentioned above, transceiver 216 may communicate with one or more networks, such as the Internet, also referred to as the World Wide Web (WWW), an intranet and/or a wireless network, such as a cellular telephone network, a wireless local area network (LAN), and/or a metropolitan area network (MAN), and other devices. Mobile device 120 may use any of a plurality of communications standards to communicate to networks or other devices with transceiver 216. Communications standards, protocols and technologies for communicating include, but are not limited to, Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth®, Wireless Fidelity (Wi-Fi) (e.g., IEEE 202.11a, IEEE 202.11g and/or IEEE 202.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol.

Transceiver 216 may also be configured to assist mobile device 120 in communicating with one or more sensors 108 (FIG. 1). For example, transceiver 216 can be directed to provide signals that are suitable for determining the existence and availability of sensors 108. As shown in FIG. 2A, mobile device 120 can indicate that it is searching for sensors 108 and relevant information (e.g., heart rate). Mobile device 120 can also request input from the individual as to whether or not the sensors are properly placed at interface object 220". The individual can then indicate, using touch-screen 204 or other means, such as voice activation, that the sensors 108 are in place and activated.

Mobile device 120 may also include other applications or programs such as, but not limited to, word processing applications, JAVA-enabled applications, encryption, digital rights management, voice recognition, voice replication, and a browser module. The browser module may be used to browse the Internet, including searching, linking to, receiving, and displaying web pages or portions thereof, as well as attachments and other files linked to web pages.

It should be appreciated that the mobile device 120 is only one example of the mobile device that may be used with the present system and method, and that the mobile device may have more or fewer components than mentioned, may combine two or more components, or may have a different configuration or arrangement of the components In the present system and method, mobile device 120 may be implemented with any computing device that includes virtual reality functionality and is not so large that it is very inconvenient to move it from one location to another. Thus, mobile device 120 is not restricted to a smartphone or other hand-held device, and may include pad or tablet computing devices, smart books, net books, laptops, watches, and even larger computing devices with virtual reality functionality that may be moved from one location to another without significant inconvenience.

Sensor 108 is designed and configured to measure a physiological parameter of the individual using the BVRS 100 and to send a signal, representative of the measurement, to portable computing device 104. Sensor 108 is electronically coupled to portable computing device 104, which as is known in the art, can be a wired or wireless connection. At a high level, sensor 108 can be any sensor (or combination of sensors) capable of providing information sufficient to determine an individual's heart rate and/or RR interval. In exemplary embodiment, sensor 108 is an ear clip sensor (sensor 108A) suitable for measuring an individual's heart rate and/or RR interval and is positioned on the individual's ear lobe. In another exemplary embodiment, sensor 108 is a chest strap sensor (sensor 108B) suitable for measuring an individual's heart rate and/or RR interval and is fastened around the individual's chest. Other sensor technologies capable of measuring heart rate and/or RR Interval, as are known in the art, can be substituted for sensors 108A and 108B.

Returning to FIG. 1, virtual reality headset 112 is capable of providing an immersive virtual reality environment to the individual using BVRS 100. Virtual reality, as is known in the art, can be referred to as immersive multimedia or computer-simulated reality, and attempts to simulate a physical presence in places in the real world or an imagined world, allowing the user to interact in that world, and can, in certain embodiments, create sensory experiences, which can include sight, hearing, touch, and smell. In an exemplary embodiment, and as shown in FIG. 1, virtual reality headset 112 can include a mounting area 124, a viewing area 128, control knobs 132, and a head strap 136. In this embodiment, mounting area 124 is sized and configured to accept a device, such as smartphone 120 or other portable computing device, which as described above, includes portable computing device 104. Viewing area 128 is sized and configured to allow for viewing of the device contained in mounting area 124. When BVRS 100 is in use, mounting area 124 is coupled to viewing area 128. Control knobs 132 can control the output of smartphone 120 (or another portable computing device) and/or adjust the relationship between viewing area 128 and mounting area 124 (allowing the user to focus the image, much like adjusting a pair of binoculars). In the embodiment shown in FIG. 1, an individual uses head strap 136 to secure BVRS 100 to the user's head and face.

Although BVRS 100 has been described above as having a separate portable computing device 104 and virtual reality headset 112, it is understood that these two components could be integrated into a single device or unit.

Virtual reality headset 112 can also include a variety of features, which can be provided with the virtual reality headset 112 or the portable computing device 104 when they are connected and in communication with one another. For example, each device may include one or more of the following components: processors, display screen, controls (e.g., buttons, switches, touch pads, and/or screens), camera, receiver, antenna, microphone, speaker, batteries, optical subassembly, sensors, memory, communication systems, input/output ("I/O") systems, connectivity systems, cooling systems, connectors, and/or the like. If activated, these components may be configured to work together or separately depending on the needs of the system. In some cases, features may be turned off entirely if not needed by the system.

Figure 3:
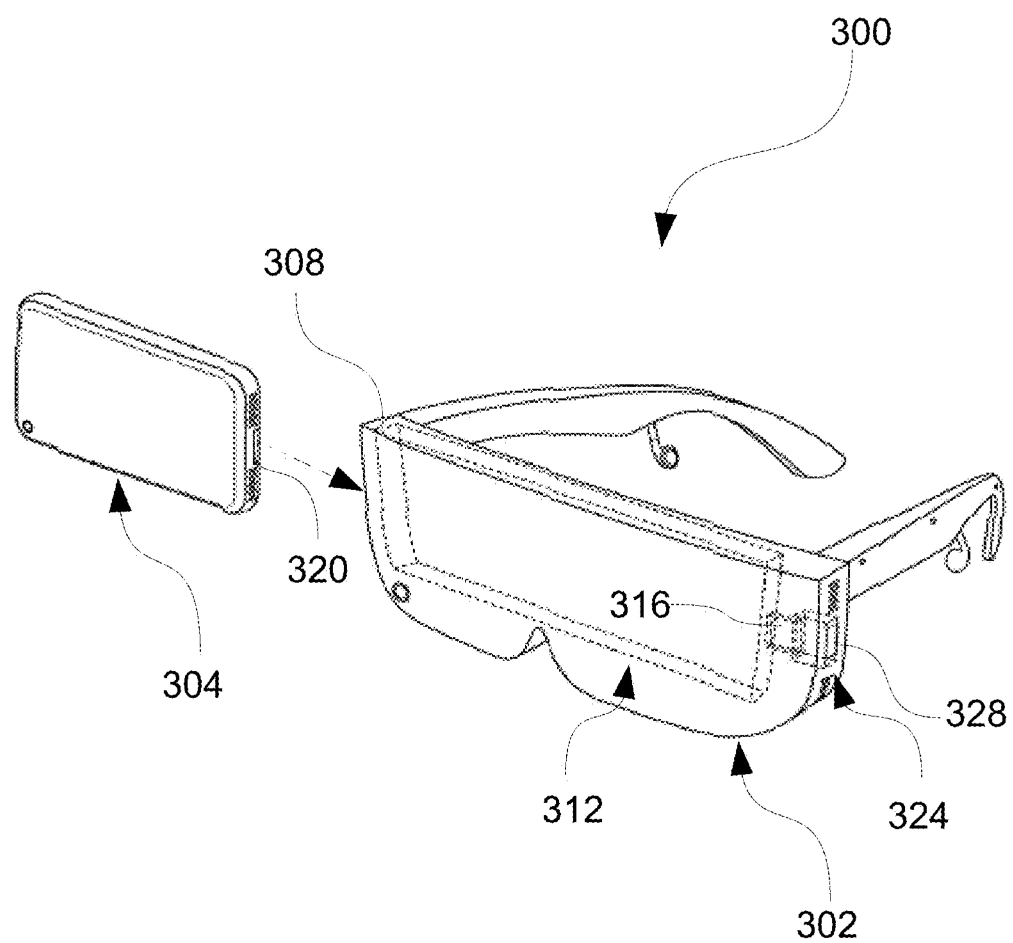
FIG. 3 is a perspective view of another biofeedback virtual reality system according to an embodiment of the present invention.

FIG. 3 shows another embodiment of a BVRS, BVSR 200, having a virtual reality headset 302 in combination with a portable computing device 304. In this embodiment, portable computing device 304 is releasably slidably engageable with virtual reality headset 302. As shown in FIG. 3, virtual reality headset 302 has portable computing device 304 which is slid through a slot 308 in virtual reality headset 302 and into a cavity 312 sized and configured to accept portable computing device 304. Slot 308 may be situated opposite a headset connector 316 such that as portable computing device 304 is slid into cavity 312, device connector 320 (associated with portable computing device 304) can mate with headset connector 316.

Headset connector 316 and device connector 320 can allow data and/or power communications between virtual reality headset 302 and portable computing device 304. Headset connector 316 and device connector 320 can take on a number of different forms, such as, but not limited to, low profile connectors, USB, micro-USB, FireWire, or a 30 pin connector used in iPods™ and iPhones™ manufactured by Apple Inc. of Cupertino, Calif. In some cases, the cavity/connector combination may generally define a docking station for portable computing device 304.

Because device connector 320 may be blocked once portable computing device 304 is coupled to virtual reality headset 302, the portable computing device may be prevented from interfacing with other devices. To accommodate other devices, virtual reality headset 302 can include an adaptor 324 that includes an exterior connector 328 on the outside of the virtual reality headset. As a result, when another device (e.g., a battery) is plugged into exterior connector 328, this device can interface with portable computing device 304.

After coupling portable computing device 304 to virtual reality headset 302, the protocol under which devices communicate may be widely varied. Any suitable communication protocol may be used, such as, for example, a master/slave communication protocol, server/client communication protocol, peer/peer communication protocol, or any combination thereof. For example, using a master/slave communication protocol, one of the devices, the master device, controls the other device, the slave device. For instance, the portable computing device 304 may become a slave to the virtual reality headset 302 such that the head-mounted device controls the operation of the portable electronic device after coupling. Alternatively, the virtual reality headset 302 can serve as a slave of the portable computing device 304 by simply implementing actions based on controls from the portable computing device. As another example, using a client/server communication protocol, a server program, operating on either portable computing device 304 or virtual reality headset 302, responds to requests from a client program. As yet another example, using a peer to peer communication protocol, either of the two devices can initiate a communication session.

Generally, the communication session can begin when portable computing device 304 and virtual reality headset 302 are coupled together. In some cases, the devices may switch immediately into a virtual reality mode once connected. In the virtual reality mode, the size and possibly the resolution of one or more image frames on the screen may be adjusted for viewing at close proximity. In addition, some features can be turned on/off while the settings of other features may be reconfigured differently from normal portable computing device 304 use. For example, input devices, output devices, sensors, and other electrical systems can be activated or deactivated based on the default settings.

In one embodiment, an individual may be provided with an option to set up the virtual reality display system manually. For example, the user may be prompted with a control menu (such as the user interface 500 shown in FIG. 5) for setting up the virtual reality display system when the devices are coupled together. As another example, the user may be provided with an option to manually set the distance between two image frames that are displayed on the screen (one for each eye). For example, the user may select a control (e.g., rotate a knob, such as control knob 132 (FIG. 1)) to align the two image frames with his eyes.

Alternatively, if adjustments are difficult for the user, portable computing device 304 and/or virtual reality headset 302 may include mechanisms for automatically configuring the image frame location and size based on default settings. As should be appreciated, each user of BVRS 100 or 200 will have eyes that are arranged differently. For example, some eyes are located close together while others are more spread out. Thus, either device may include sensors for detecting the distance to the eyes and the position of the eyes. After determining the optimal viewing positions and size of the displayed image frames based on the detected distance and position, BVRS 300 can adjust the viewing positions.

The resolution of the displayed image frames can also be adjusted in a similar manner. However, because each user's eyes focus differently, it may be beneficial to allow the user to manually adjust the resolution, such as using control knobs 132 (FIG. 1). In an exemplary embodiment, BVRS 300 can include a sensing mechanism for alerting the portable computing device 304 that the device has been coupled to the virtual reality headset 302. As a result, portable computing device 304 can switch to the virtual reality mode. By way of example, the sensing mechanism may be an electrical connection, a sensor such as a proximity sensor or IR detector, and/or the like. The sensing mechanism may be used instead of or in combination with the communication interface to assist the devices in switching to the virtual reality mode.

In addition, as a result of operatively coupling the devices through wired and/or wireless interfaces, features of the virtual reality headset 302 may be extended to the portable computing device 304, and features of the portable computing device may be extended to the virtual reality headset.

Figure 4:
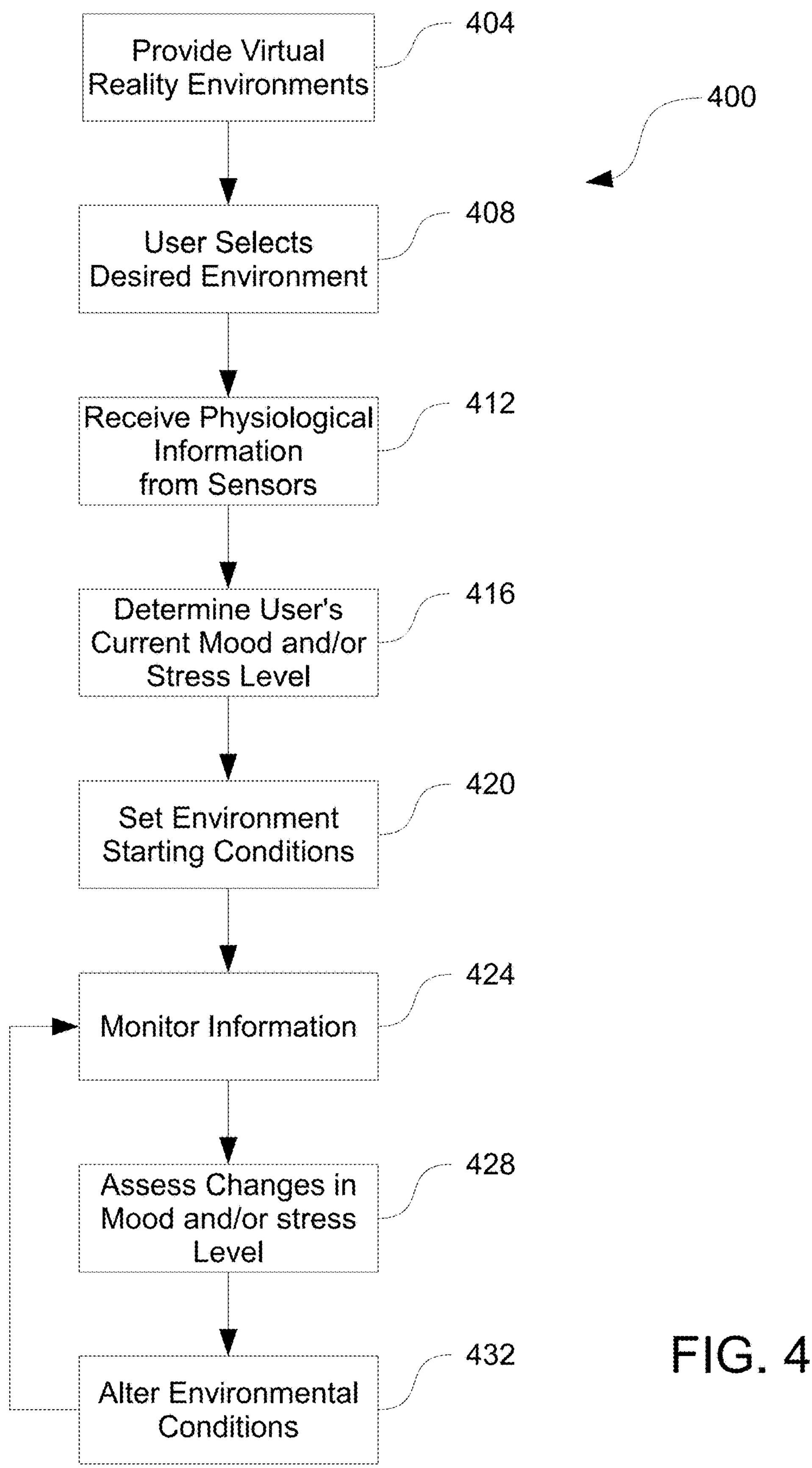
FIG. 4 is a block diagram of an exemplary process for improving a user's mental state according to an embodiment of the present invention.
Figure 5:
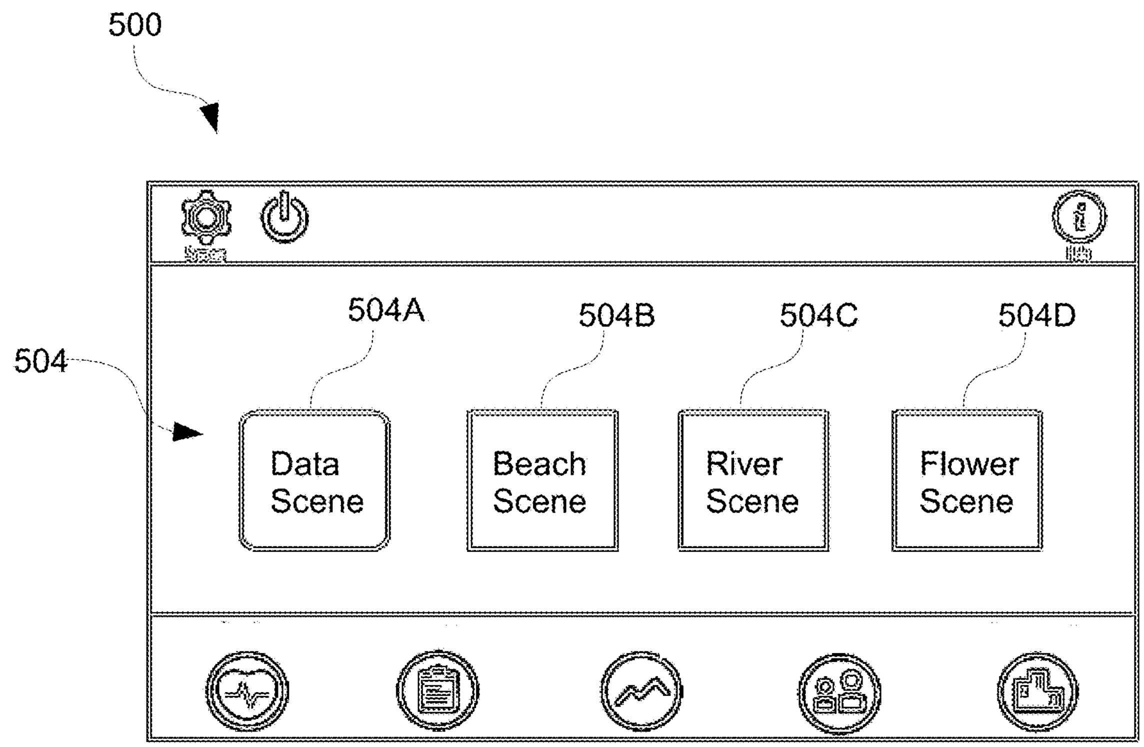
FIG. 5 is an illustration of a user interface suitable for use with a biofeedback virtual reality system according to an embodiment of the present invention.
Figure 6:
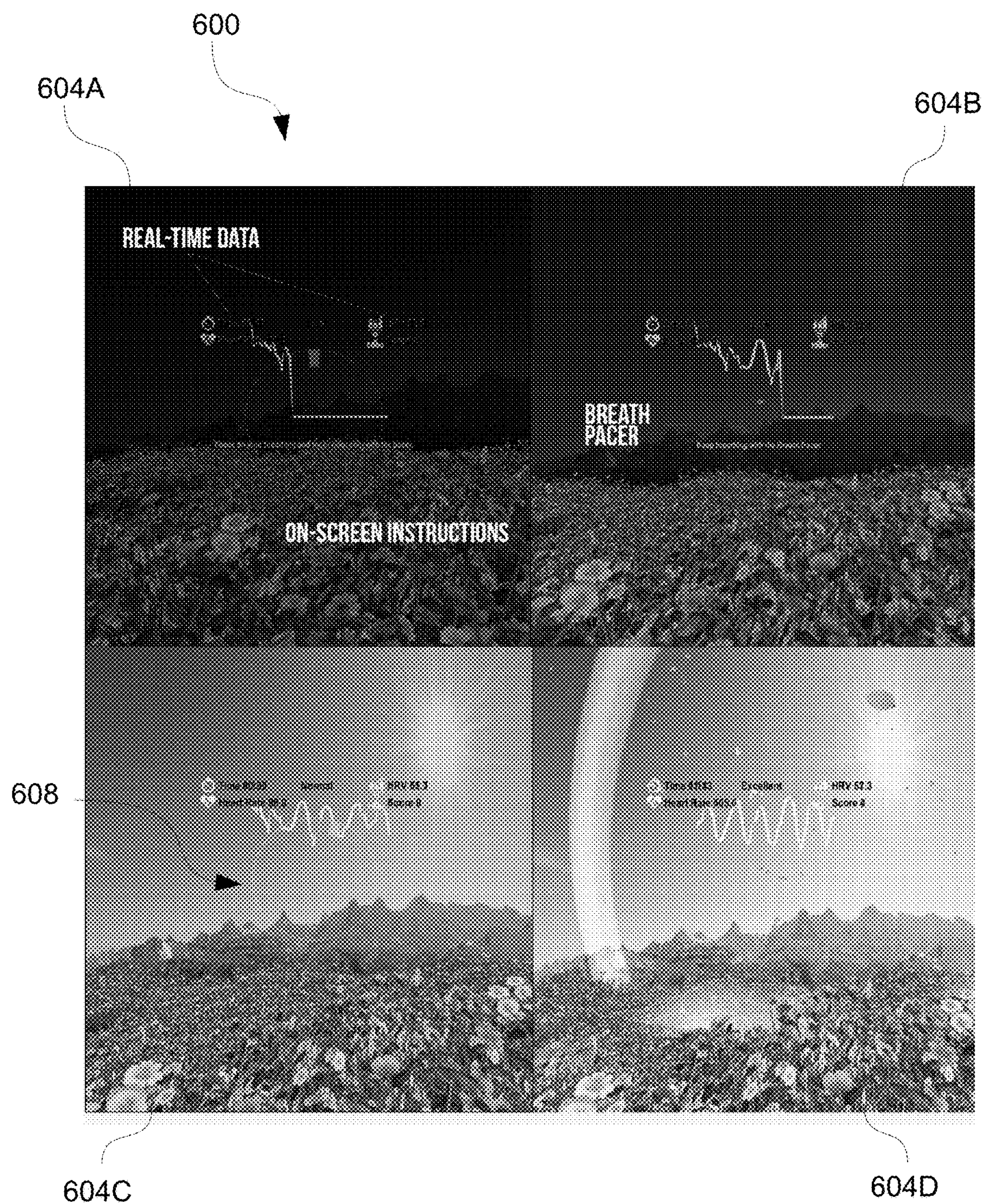
FIG. 6 is a diagram of an exemplary biofeedback virtual reality display showing the change in the virtual reality environment as coherence is achieved.

Turning now to FIG. 4, and with reference to FIGS. 5 and 6, there is shown an exemplary biofeedback virtual reality process 400 suitable for use with a biofeedback virtual reality system such as BVRS 100 or BVRS 300.

At step 404, the user is provided with a plurality of virtual reality environments to select from. An exemplary user interface 500 for the selection of virtual reality environments 504, also referred to as "scenes", is shown in FIG. 5. Virtual reality environments 504 can include, but are not limited to, a data scene 504A, a beach scene 504B, a river scene 504C, and a flower scene 504D. Additional or different scenes may be provided to the user. Typically, as a biofeedback virtual reality system as described herein is intended to calm and improve the coherence of the user, virtual reality environments 504 are designed to induce calm. However, it is understood that a user may desire to challenge themselves to remain calm under more stressful conditions and as such, virtual reality environments 504 can be designed to present stressful situations and conditions, for example, driving in busy traffic conditions, helping a crying baby, or being out in stormy weather. In this way, a user may be able to improve their ability to respond to calamitous conditions from the safety of a controlled environment.

At step 408, the user selects the desired virtual reality environment. As discussed herein, selection of the environment can be done in varied ways, for example, by eye command, voice command, by remote control, or through an input device, such as input device 208.

At step 412, physiological information from one or more sensors, such as sensor 108, is received. Typically, the information received from the sensor(s) is signals indicative of a heart rate and RR interval, although other sensors may be used as desired. For example, a breath monitor may be used to identify when a user has taken a breath, the duration of the breath, the intake and release portions of the breath cycle, whether the user has held their breath for any period of time, etc.

Based upon the physiological information received at step 412, a user's current mood and/or stress level, i.e., coherence, are determined at step 416. In an exemplary embodiment, the user's current mood and/or stress level are determined by their HRV (duration between heart beat peaks in milliseconds also referred to as RR intervals). The RR interval is used to determine a frequency of heart rate variability (FHRV) using Equation 1. where the RR interval is measured in milliseconds:

FHRV(Hz)60.0/(Current RR Interval/1000).

As HRV has cyclic behavior, the FHRV is then used to determine an HRV score, which is an analysis of the number of HRV cycles per minute. In an exemplary embodiment, the beginning and end of a cycle is determined by evaluating the difference between sequential FHRV determinations, e.g., $FHRV_n - FHRV_{n+1}$. A change in the sign of the aforementioned difference, e.g., positive to negative, indicates the beginning of a cycle, and, upon the next occurrence of the same sign change, i.e., positive to negative, in this example, indicates the end of a cycle. In general, the higher the number of cycles, which corresponds to a lower HRV score, the more anxious or stressed a person is presumed to be, whereas a lower number of cycles (higher HRV score) is indicative of calmness and control.

In another exemplary embodiment, the HRV score (and thus the determination as to the individuals' stress/coherence) is a function of the inverse of the root mean square standard deviation of the FHRV. In another exemplary embodiment, HRV data is used to derive a respiratory rate via methodologies known in the art.

At step 420, the virtual reality environmental starting conditions are set. For example, if a user has chosen a flower scene (at step 408) (as shown in FIG. 6 as scene 600) and the individual is measured to have a relatively low HRV score (at step 416), the environmental starting conditions can be a dark, placid, soundless landscape (upper left block 604A), with the desired outcome being to provide an influence to induce calm in the user. Alternatively, if the user has chosen a flower scene and has a relatively high HRV score, the starting conditions may be the flower field at daybreak (upper right block 604B) with slight rustling of leaves and the sounds of birds. It should be recalled that the goal is not to have the highest HRV score possible, but to obtain coherence or resonance, which is a controlled conjoining of the body's natural frequencies. Thus, having an HRV that is too high, would likely avoid achieving the desired resonance.

In any of the scenes, a breath indicator can be provided that assists the individual with maintaining a desired breathing rhythm. For example, in one embodiment an indicator is shown that prompts the user to take a breath. The timing sequence of the indicator can be a function of a predetermined optimal number of breaths for the individual. By way of a non-limiting example, if the predetermined optimal number of breaths is determined to be 6 breaths per minute, then the timing sequence for the breathing indicator would be set to 10-second intervals. Thus, in this case an individual would be provided with a breath indicator at each 10-second interval such that a total of breaths would be taken each minute. It should of course be appreciated that the predetermined optimal number of breaths per minute may be more or less than 6. While the breath indicator may provide any type of indication capable of perception using one or more of the human senses, in one embodiment, a breath indicator is a light that is visible to a given subject, such that the user knows when to take a breath. It should similarly be appreciated that any other visual, audio, or sensory prompt may be used. Although not necessary, a breath monitor can be included to more accurately track the user's breathing rhythms.

If a breath monitor is used, in order to substantially optimize a subject's respiratory cycle, the individual's reaction time to the breathing stimulus may also be taken into account. That is, the time between when the breath indicator is provided to the individual and the time when the individual actually takes a breath may vary by 1-2 seconds. Moreover, reaction times tend to vary between individuals. Accordingly, the training system may be calibrated based on a particular individual's reaction time. In one embodiment, a calibration mode is used to determine an approximation of a given individual's reaction time. During this calibration mode, a series of breath indications are provided to the individual. The length of time between when the breath indications are provided and when the individual actually takes a breath may then be measured. This value is then incorporated into the indicator timing sequence to ensure that the optimal number of breaths per given time period (e.g., per minute) are taken.

Returning to FIG. 4, at step 424, the individual's physiological information is monitored (via, as before, sensors, such as sensor 108) so as to provide guidance and feedback that is correlated to the individual's heart rate or HRV at step 428. In an exemplary embodiment, a target pattern is provided that is a sine wave of an optimized heart-rate/HRV rhythm that the individual's heart rate/HRV rhythm should attempt to match by modifying their breathing and/or other physiological changes (relaxing the body, clearing the mind, etc.). In another exemplary embodiment, the breathing rhythm indicator may begin at a pace that is only slightly slower than a preliminary breathing pattern (based upon heart rate and/or HRV values), and is slowly modified to reach the target pattern as the individual's heart rate and/or HRV values improve. In another exemplary embodiment, a virtual reality scene can additionally include a target pattern (e.g., a sine wave) that can converge onto the optimized frequency as the individual's "coherence peak" is maximized—in other words, the user is driven toward a goal and with improved heart rate and/or HRV the user edges closer to that goal. When the coherence peak reaches its maximum, the frequency would be the natural resonant frequency that would become the target rhythm that may then be displayed to the individual for training purposes.

At step 432, as the individual's heart rate and HRV reaches a more desirable level, the conditions of the virtual reality environment change. As shown in FIG. 6, a flower scene can change from a dark, placid environment (upper left block 604A) to a bright, sunny, with a rainbow environment (lower right block 604D) as a user progresses.

In use, a user initiates process 400, via a mobile device such as mobile device 120, and straps the heart rate monitor across the chest or attaches the ear-clip sensor to one of the earlobes. From a main user interface 500 (FIG. 5), a user can select one of several virtual reality scenes (scenes 504A-D). The user can then be asked to breathe in sync with a breath indicator 608 (example shown in FIG. 6) that grows and contracts in the middle of the screen. Mobile device 120 then receives a signal, representative of heart rate information, e.g., pulse information and RR interval information, from sensor 108, determines the user's HRV in real time and develops an HRV score, and uses the HRV score to determine the user's state of coherence and to set the conditions of the virtual reality scene. Mobile device 120 can provide on-screen instructions to the user to help the user achieve a higher state of coherence. Mobile device 120 can then make real-time changes to the immersive virtual reality environment to reflect the changes in the user's state of coherence (other scenes in FIG. 6.) To exit the virtual reality environment, the user can interact with the mobile device 120 using input device 208, and mobile device 120 can display the user's session results, such as HRV, average heart beats per minute, Root Mean Square of the Successive Differences, etc.

In another embodiment, the biofeedback virtual reality system will challenge the user by offering stressful situations in the VR environment to test the user to maintain coherence. The VR environment may be suspenseful, worrisome, exciting, thrilling, etc., and may be chosen by the user and may have alternative and increasingly difficulty levels of VR scenes.

Figure 7:
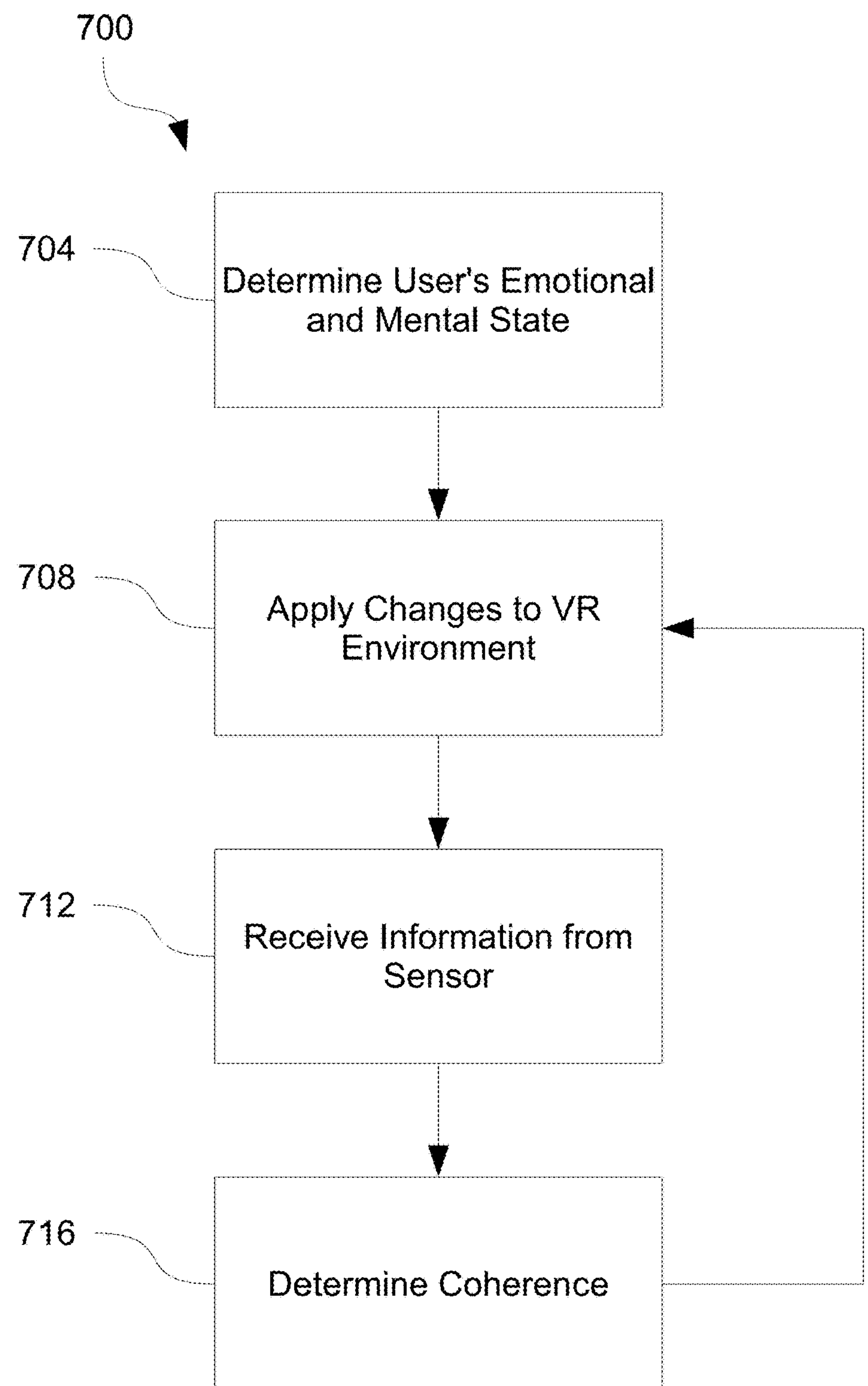
FIG. 7 is a block diagram of another exemplary process for improving a user's mental state according to an embodiment of the present invention.

Turning now to FIG. 7, another exemplary process 700 for use within a BVRS is shown. At step 704, a determination of the user's mental and emotional state—e.g., understanding the current coherence of the user—is completed. In this step, the mobile device, such as mobile device 120, may be calibrated to take into account the reaction times of the particular individual. In one embodiment this is done by providing the individual a breath monitor and series of test indicators are then given to the individual. The individual is asked to breathe each time they receive a test indicator. The time that lapses between when the test indicators are provided and when the individual actually takes a breath is measured for each iteration of the test. Thereafter, some measure of the mean or average reaction time is determined. It should be appreciated that numerous methods may be used to arrive at a reaction time for the individual including, but not limited to, the mean, average, weighted average, etc.

At step 708, the user may select the virtual reality scene, which may have initial conditions that are influenced by the calibrations or other information (e.g., current heart rate, current RR interval, etc.). In any event, the heart rate training sequence begins by providing a heart rate indicator to the individual and continued monitoring (via, for example, sensor 108) of the heart rate of the user at step 712.

In another exemplary embodiment, prior to beginning the training, a user can select from several levels of difficulty and can receive a score, which is based, at least in part, on the level of difficulty chosen. After completing a training session the user's score may be visible to a local or global leaderboard. In another embodiment, the user forms a team with other users, either locally or disparately located, and team scores are comparable. In an exemplary embodiment, teams include between 3 and 9 users, although more users are possible.

At step 716 the user's coherence is determined using methods discussed herein. As the user's coherence changes, the imagery shown in the virtual reality scene is modified—such as by the scene changes shown in FIG. 6 (note scene improvements from top left to bottom right). This feedback is indicative of the individual's respiratory cycle and/or respiratory sinus arrhythmia (RSA) pattern approaching the optimal level, with the individual's heart rate and/or RR interval being the physiological measurements that provide an indication of the individual's breathing rhythms. In one embodiment, a graphical element that transitions toward a goal may be displayed to the individual as the optimal heart rate level is approached. By way of example, FIG. 6 is a presentation format produced by the training system in accordance with one embodiment of the invention.

It should of course be appreciated that numerous other forms of positive feedback may also be provided to the individual as the optimized respiratory cycle and/or RSA pattern is approached. Such other forms of positive feedback may include audible feedback, tactile feedback, etc.

Alternate embodiments may employ a variety of display formats including detailed information, graphical information, graphic images, video images, and audio feedback. Similarly, coherence, as derived from heart rate or RR intervals may be used to drive audio, video and/or specific gaming events. In particular, a decrease in coherence (which is associated with a negative mental/emotional state) would generate one type of feedback or gaming event, while an increase in coherence (associated with a positive mental/emotional state) would drive a difference type of feedback or gaming event.

Figure 8:
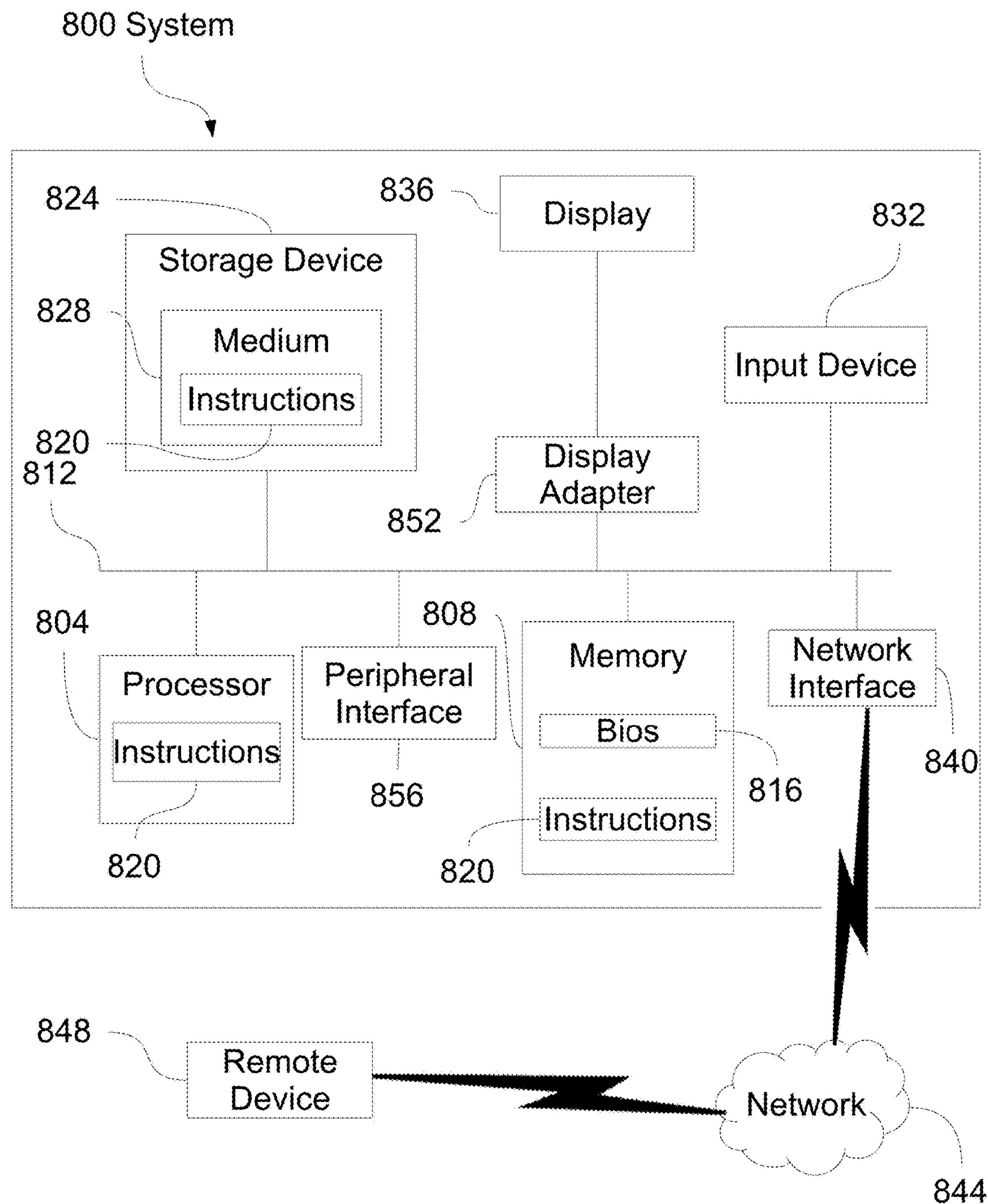
FIG. 8 is an exemplary computing system for use with a biofeedback virtual reality system according to an embodiment of the present invention.

FIG. 8 shows a diagrammatic representation of one embodiment of a computing system, e.g., mobile device 120, in the exemplary form of a system 800, within which a set of instructions for causing a processor 804 to perform any one or more of the aspects and/or methodologies, such as process 400 or 700, of the present disclosure. It is also contemplated that multiple computing devices, such as mobile devices 120, or a combination of the mobile device and virtual reality headset 112, may be utilized to implement a specially configured set of instructions for causing a BVRS, such as BVRS 100 or 300, to perform any one or more of the aspects and/or methodologies of the present disclosure.

System 800 can also include a memory 808 that communicates with other components, via a bus 812. Bus 812 may include any of several types of bus structures including, but not limited to, a memory bus, a memory controller, a peripheral bus, a local bus, and any combinations thereof, using any of a variety of bus architectures.

Memory 808 may include various components (e.g., machine readable media) including, but not limited to, a random access memory component (e.g., a static RAM "SRAM", a dynamic RAM "DRAM", etc.), a read only component, and any combinations thereof. In one example, a basic input/output system 816 (BIOS), including basic routines that help to transfer information between elements within system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

System 800 may also include a storage device 824, such as, but not limited to, the machine readable storage medium described above. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with system 800 (e.g., via an external port connector (not shown)). Particularly, storage device 824 and an associated machine-readable medium 828 may provide nonvolatile and/or volatile storage of machine-readable instructions, data structures, program modules, and/or other data for system 800. In one example, software 820 may reside, completely or partially, within non-transitory machine-readable medium 828. In another example, software 820 may reside, completely or partially, within processor 804.

System 800 may also include an input device 832. In one example, a user of system 800 may enter commands and/or other information into system 800, for example using input device 208, via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), touch screen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above. Input device can also include sensors 108 and other sensors or monitors discussed herein.

A user may also input commands and/or other information to system 800 via storage device 824 (e.g., a removable disk drive, a flash drive, etc.) and/or network interface device 840. A network interface device, such as network interface device 840 may be utilized for connecting system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network, a telephone network, a data network associated with a telephone/voice provider, a direct connection between two computing devices, and any combinations thereof. A network, such as network 844, may employ a wired and/or a wireless mode of communication. In general, any network topology may be used. Information (e.g., data, software 820, etc.) may be communicated to and/or from system 800 via network interface device 840.

System 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. In addition to a display device, a system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A biofeedback virtual reality system comprising:
- a virtual reality headset having a viewing area for a user;
- a sensor, the sensor producing a signal indicative of a physiological parameter of the user;
- a portable computing device coupled to the virtual reality headset and electronically coupled to the sensor, the portable computing device configured to receive the signal and including a processor and a memory, the memory including a plurality of virtual reality environments and a set of instructions executable by the processor, the instructions including;
  - determining the mental state of the user based upon the signal;
  - selecting a one of the plurality of environments based on the determined mental state;
  - delivering the selected one of the plurality of environments to the user on the viewing area;
  - adjusting the selected one based upon the determining, wherein the adjusting is in the form of setting a plurality of initial conditions associated with the selected one of the virtual reality environments;
  - monitoring the signal; and
  - altering the selected one of the plurality of environments based upon the monitoring.

2. A biofeedback virtual reality system according to claim 1, wherein the physiological parameter is an RR interval.

3. A biofeedback virtual reality system according to claim 2, wherein the portable computing device receives the signal and determines a coherence, the coherence influencing the altering.

4. A biofeedback virtual reality system according to claim 2, wherein the sensor is included in a chest strap monitor.

5. A biofeedback virtual reality system according to claim 2, wherein the sensor is included in an ear clip monitor.

6. A biofeedback virtual reality system according to claim 1, wherein the virtual reality headset has a mounting area sized and configured to accept the portable computing device.

7. A biofeedback virtual reality system according to claim 1, wherein the virtual reality headset and portable computing device are integrally connected so as to form a single unit without the ability to remove the portable computing device.

8. A biofeedback virtual reality system according to claim 1, wherein the set of instructions further includes providing a breath indicator in the viewing area, the breath indicator prompting the user to take a breath at predetermined times.

9. A biofeedback virtual reality system according to claim 8, further including a breathing monitor suitable for monitoring the breathing of the user and wherein the instructions further include determining the user's reaction time to the prompting of the breath indicator.

10. A biofeedback virtual reality system according to claim 9, wherein the set of instructions further includes incorporating the reaction time into the predetermined times for prompting.

11. A biofeedback virtual reality system comprising:
- a sensor configured to produce a first signal representative of a user's heart rate and to produce a second signal representative of the time between heart beat peaks of the user; and
- a virtual reality device including a headset and a portable computing device coupled to the virtual reality headset and electronically coupled to the sensor, the portable computing device configured to receive the signal and including a processor and a memory, the memory including a plurality of virtual reality environments and a set of instructions executable by the processor, the instructions including:
  - determining the mental state of the user based upon the first signal and the second signal;
  - selecting a one of the plurality of environments based on the determined mental state;
  - delivering the selected one of the plurality of environments to the user;
  - adjusting the selected one based upon the determining, wherein the adjusting is in the form of setting a plurality of initial conditions associated with the selected one of the virtual reality environments;
  - monitoring the first signal and the second signal; and
  - altering the selected one of the plurality of environments based upon the monitoring.

12. A biofeedback virtual reality system according to claim 11, wherein the portable computing device receives the signal and the second signal and determines a coherence, the coherence influencing the altering.

13. A biofeedback virtual reality system according to claim 11, wherein the sensor is included in a chest strap monitor.

14. A biofeedback virtual reality system according to claim 11, wherein the sensor is included in an ear clip monitor.

15. A biofeedback virtual reality system according to claim 11, wherein the virtual reality headset and portable computing device are integrally connected so as to form a single unit without the ability to remove the portable computing device.

16. A biofeedback virtual reality system according to claim 11, wherein the set of instructions further includes providing a breath indicator suitable for prompting the user to take a breath at predetermined times.

17. A biofeedback virtual reality system according to claim 16, further including a breathing monitor suitable for monitoring the breathing of the user and wherein the instructions further include determining the user's reaction time to the prompting by the breath indicator.

18. A biofeedback virtual reality system according to claim 17, wherein the set of instructions further includes calibrating the prompting of the breath indicator based on the determined reaction time.

19. A method of improving a mental state of a user in need thereof, the method comprising:
- providing a virtual reality device and a sensor configured to transmit a signal representative of physiological information of the user, the virtual reality device including a plurality of virtual reality environments;
- determining a current mental state of the user based upon the signal;
- setting an initial state of a selected one of the plurality of virtual reality environments based upon the determining;
- providing a breath indicator, the breath indicator indicating when the user should attempt to take a breath;
- monitoring the mental state of the user via the sensor; and
- adjusting the state of the selected one of the plurality of virtual reality environments, from the initial state, based upon the monitoring.

20. A method according to claim 19, wherein the determining a current mental state is derived from an HRV score, which is inversely proportional to the user's HRV cycle.

* * * * *